United States Patent [19]

van Lit

[11] 4,391,781

[45] Jul. 5, 1983

[54] ELECTRICALLY HEATED VAPOR DISPENSER

[75] Inventor: Klaas J. van Lit, Amstelveen, Netherlands

[73] Assignee: S. C. Johnson & Son, Inc., Racine, Wis.

[21] Appl. No.: 360,866

[22] Filed: Mar. 22, 1982

[51] Int. Cl.³ .............................................. A61L 9/03
[52] U.S. Cl. .................................... 422/125; 219/243; 219/274; 239/136; 422/305; 422/306
[58] Field of Search .................. 422/125, 305, 306, 49; 239/136, 55, 56; 219/274, 275, 385, 386, 271, 273, 243

[56] References Cited

U.S. PATENT DOCUMENTS

| | | | |
|---|---|---|---|
| 2,513,919 | 7/1950 | Costello | 422/306 X |
| 2,931,880 | 4/1960 | Yaffe | 422/125 X |
| 2,942,090 | 6/1960 | Diehl | 422/125 X |
| 3,748,438 | 7/1973 | Costello | 422/305 X |
| 4,197,271 | 4/1980 | Fenstermaker et al. | 422/306 X |
| 4,214,146 | 7/1980 | Schimenske | 422/306 X |

FOREIGN PATENT DOCUMENTS 234954 8/1959 Australia .............................. 422/305

Primary Examiner—Barry S. Richman

[57] ABSTRACT

A device for dispensing thermally volatilizable substances of the type having a heating surface against which is placed a mat which is impregnated with a volatilizable substance. A clamp arm, which is biased toward the heating surface, presses the mat against such surface, and a lever, which is depressible, when depressed engages the clamp arm and moves it away from the heating surface, thereby releasing the mat to facilitate replacement thereof.

8 Claims, 5 Drawing Figures

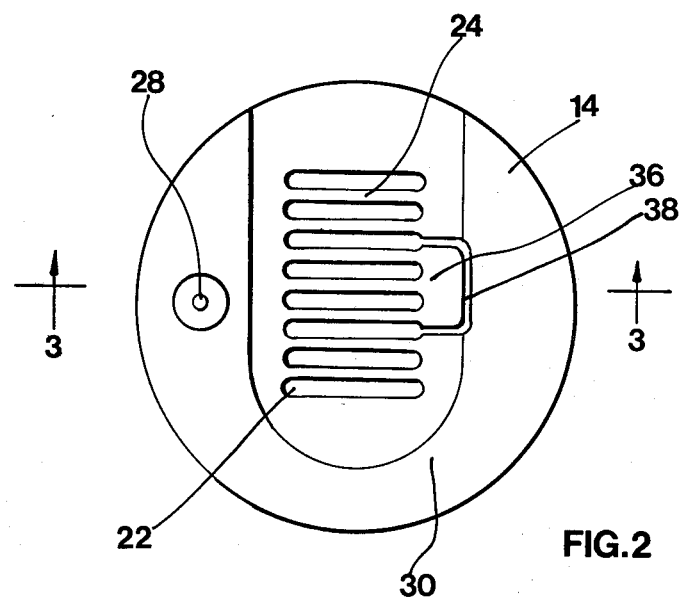
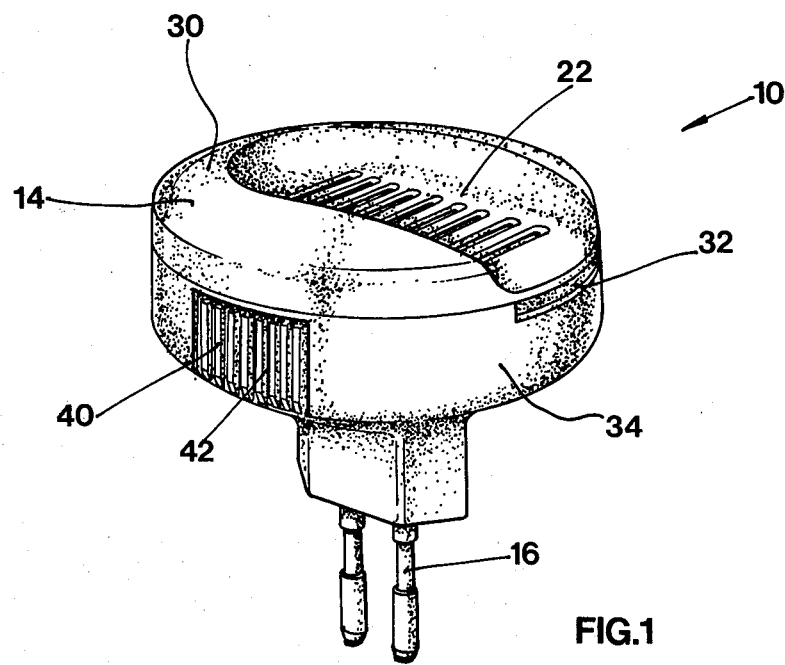

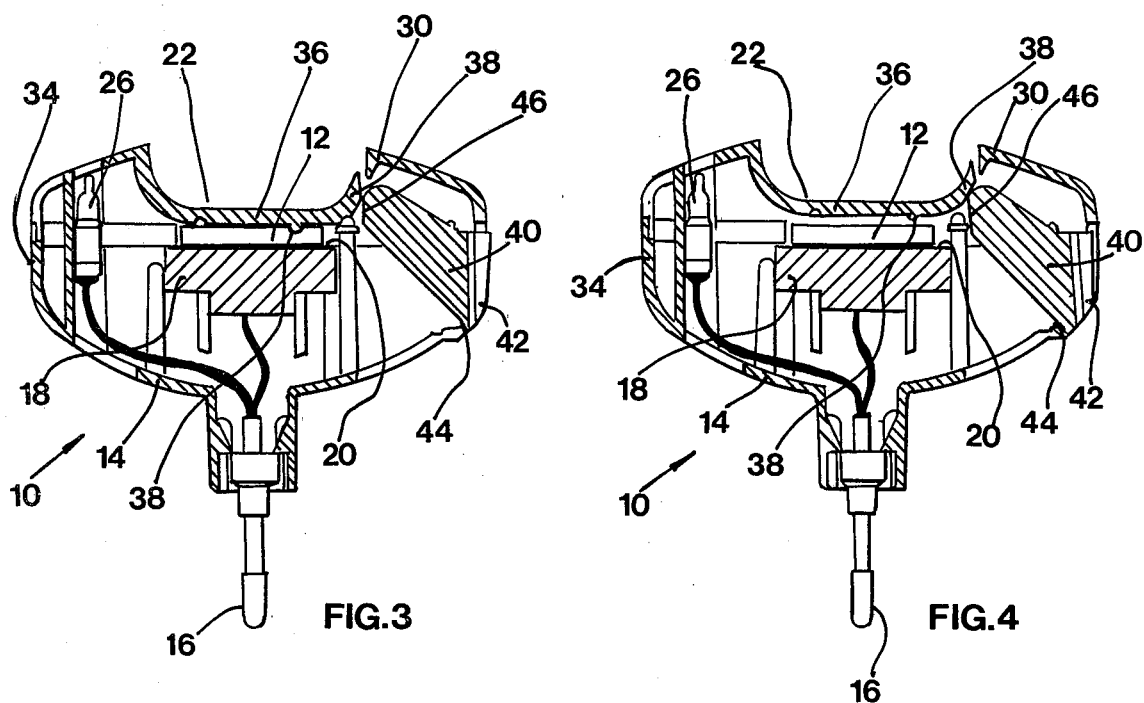
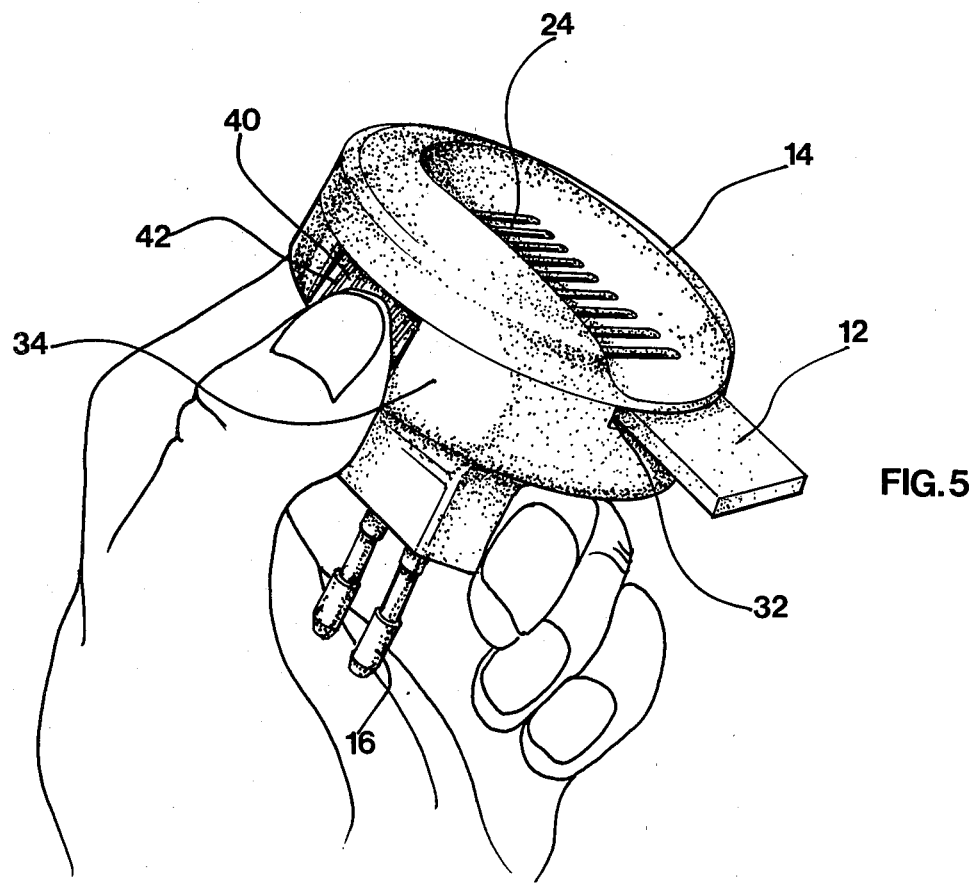

ELECTRICALLY HEATED VAPOR DISPENSER

FIELD OF THE INVENTION

The present invention relates generally to vapor dispensers and more specifically to dispensers for thermally volatilizable substances such as certain insecticides and air fresheners.

BACKGROUND OF THE INVENTION

A wide variety of dispensers for insecticide vapors, air freshener vapors, and other air-treating vapors are known in the art. More specifically, it is known to provide a dispenser in which volatilizable materials, such as certain insecticides and air fresheners, may be driven by heating from substrates in which they are contained. The substrates containing such volatilizable materials are typically small mats of cellulosic material such as paperboard. Heat is applied to such mats through an electrically heated plate against which such mats are held. A heating coil is used to heat the plate. The mats are replaceable.

The rate of vapor-dispensing in devices of the type described can vary unacceptably if the degree of contact between the mats and the heating plate varies. For example, if for a first mat there is a firm face-to-face contact with the heating plate and for a second mat the contact is relatively loose, volatilization will occur more rapidly in the first mat than in the second due to greater heat transfer.

Some devices of the prior art do not provide adequate means for causing an appropriate firm contact of such mats with the heating plate. In some cases, such devices may be designed to provide the appropriate degree of mat-plate contact only for mats of a given thickness, while thinner mats would be held in place too loosely and thicker mats might not even be properly insertable into the device. Thus, there has been a need for an improved device for holding the impregnated mats against the heating plate.

A related disadvantage in certain prior art devices is the difficulty associated with insertion and/or release of replaceable impregnated mats. Such difficulties relate not only to the thickness of such mats as described above but to the method of mat replacement. Some prior art devices require that a used mat be displaced by insertion of new mat. Such loading and unloading steps may be difficult to carry out and/or difficult for consumers to understand. There has been a need for an improved mechanism for facilitating insertion and/or release of replaceable impregnated mats.

OBJECTS OF THE INVENTION

The principal object of this invention is to provide an improved device for dispensing thermally volatilizable substances such as insecticides and air fresheners.

Another object of this invention is to provide a vapor dispenser of the type described in which the rate of vapor dispensing does not vary inordinately due to variations in the degree of contact between the impregnated mats and the heating plate.

Another object of this invention is to provide a dispenser of the type described in which there is an appropriate amount of contact between any impregnated mat and the heating plate.

Still another obect of this invention is to provide a dispenser of the type described which can readily accommodate impregnated mats of having different thicknesses without unacceptably changing the degree of contact of such mats with the heating plate.

Yet another object of this invention is to provide a dispenser of the type described which allows easy replacement of impregnated pads.

These and other objects of this invention will be apparent from the descriptions of this invention that follow.

SUMMARY OF THE INVENTION

The vapor dispenser of this invention includes a housing and a heater secured within the housing and having a heating surface or plate which forms a support for a replaceable mat containing a volatilizable substance, such as an insecticide or air freshener composition. As in certain prior devices of this general type, the housing defines a window over the heating surface and an access opening adjacent to an end of the heating surface for insertion and/or removal of the replaceable impregnated mats. A protective grid secured to the housing and spanning the window may be used.

This invention is characterized by a clamp arm which is secured to the housing, extends over the window, and terminates in a free end. The arm is biased toward the heating surface and thus serves to press a replaceable impregnated mat against the heating surface, regardless of the thickness (within certain limits) of such mat. The invention is further characterized by a lever which is secured to the housing in a position such that upon depression thereof it will engage the clamp arm free end and move the clamp arm away from the heating surface. This action serves to release a mat and/or to prepare the device to accept a new mat.

In certain preferred embodiments, the interacting surfaces of the clamp arm free end and the lever are such that depression of the lever in a first direction results in movement of the clamp arm in a direction normal to (that is, at about 90 degrees to) the direction of lever depression. For example, depression of the lever may be in a direction parallel to the clamp arm while movement of the clamp arm is in a substantially transverse direction.

In certain preferred embodiments, the clamp arm has at least one protuberance facing the heating surface. Such protuberance or protuberances will serve to engage a mat as the clamp arm holds it against the heating surface. In a highly preferred embodiment, the clamp arm forms a portion of a grid. At least a portion of the housing, the grid, the clamp arm and the lever are preferably an integrally formed piece, such as a unitary plastic molding. In such embodiments, the clamp arm may be biased toward the heating surface by virtue of the elastic memory of the plastic. Likewise, the lever may be biased to a non-depressed position by the elastic memory of the plastic material.

The vapor dispensing device of this invention can accommodate replaceable impregnated mats of varying thickness. Mats of differing thickness will be held firmly against the heating surface to provide substantially steady heat transfer between the heating surface and the pad and, thus, substantially steady emission of vapors to the surrounding air.

The vapor dispensing device of this invention also allows easy insertion and release of replaceable impregnated mats. To replace a mat, the user will depress the lever while holding the entire device in his hand. Upon depressing the lever, the used mat will fall out of the access opening and a new mat can be dropped into place. Thereafter, the lever is released, allowing the clamp arm to return to its normal position in which the mat is held firmly against the heating surface.

BRIEF DESCRIPTION OF THE DRAWINGS

FIG. 1 is a perspective view of a preferred electrically heated vapor dispenser in accordance with this invention.

FIG. 2 is a top plan view of the device of FIG. 1.

FIG. 3 is a side sectional view taken along section 3—3 as shown in FIG. 2.

FIG. 4 is a side sectional view as in FIG. 3, but showing the device in a pad-releasing mode.

FIG. 5 is a perspective showing the device during release of an exhausted pad.

DETAILED DESCRIPTION OF PREFERRED EMBODIMENTS

The drawings illustrate a vapor dispenser 10 which is used for dispensing a thermally volatilizable substance. The substance, which may be an insecticide, an air freshener, or other composition, is contained within a mat 12 which is replaceably inserted within vapor dispenser 10.

Vapor dispenser 10 includes a housing 14 and a two-pronged plug 16 suitable for insertion in an electrical outlet, such as a wall outlet. Housing 14 includes a top surface 30 and a generally cylindrical sidwall surface 34. Vapor dispenser 10 includes a heater 18 mounted in fixed position within housing 14. Heater 18 has a heating surface 20 positioned to support mat 12 thereon. Housing 14 includes a window 22 over heating surface 20 and mat 12. Window 22 is covered by a protective grid 24 spaced from heating surface 20 by an amount about equal to the thickness of a mat 12, preferably slightly greater than the thickness of mat 12.

An indicator light 26, shown in FIGS. 2-4, is exposed through an opening 28 on top surface 30 of vapor dispenser 10. Indicator light 26 is electrically wired with plug 16 and heater 18 such that it is lit when the device is in use.

Housing 14 includes an access opening 32 in sidewall 34 and adjacent to one end of heating surface 20 and window 22. Mats 12 are inserted into and removed from vapor dispenser 10 through access opening 32 by movement along a line generally parallel to top surface 30 and perpendicular to the bars of protective grid 24.

Secured to housing 14 and extending over window 22 is a clamp arm 36 which forms a part of protective grid 24. Clamp arm 36 terminates in a free end 38 and is biased toward heating surface 20 at least to an extent allowing it to press a mat 12 firmly against heating surface 20. As shown in FIGS. 3 and 4, clamp arm 36 has one or more protuberances 39 which engage an inserted mat and hold it firmly in position against heating surface 20. Clamp arm 36 is integrally formed with housing 14.

A release lever 40 is secured to housing 14 in a position centered about 90° around sidewall 34 from access opening 32. Release lever 40 is configured and positioned to interact with free end 38 of clamp arm 36. Like clamp arm 36, release lever 40 is integrally formed with housing 14.

Release lever 40 has a finger depression surface 42 generally aligned with sidewall 34 of housing 14. When finger depression surface 42 is depressed, as illustrated in FIGS. 4 and 5, release lever 40 pivots slightly about pivot point 44 such that the end 46 of release lever 40 wedges free end 38 of clamp arm 36 to lift clamp arm 36 away from heating surface 20. While clamp arm 36 is moved and held away from heating surface 20, a mat 12 may be inserted into or released from the operative position on heating surface 20 beneath protective grid 24. When finger depression surface 42 is released, as shown in FIG. 3, clamp arm 36 will move back toward heating surface 20 and hold mat 12 firmly in operative position thereon.

The wedging action which allows displacement of clamp arm 36 away from heating surface 20 is facilitated by the shaping and placement of free end 38 of clamp arm 36 and lever end 46 of release lever 40. As illustrated in FIG. 4, free end 38 and lever end 46 are curved and positioned such that depression of finger depression surface 42 results in movement of clamp arm 36 in a direction normal to the direction of such depression.

Clamp arm 36, protective grid 24, release lever 40 and a portion of housing 14 are preferably integrally formed, preferably of resilient plastic materials such as nylon or polypropylene. The complete housing is preferably formed of two plastic pieces which may be snapped together after assembly with the electrical components. A wide variety of plastic materials and other materials could be used and appropriate materials would be well-known to those skilled in the art. Heater 18 is preferably made of a ceramic piece incorporating an electrical resistance unit. Heating surface 20 of heater 18 is preferably a smooth surface facilitating insertion and release of mats 12.

While in the foregoing specification this invention has been described in relation to certain preferred embodiments and many details have been set forth for purpose of illustration, it will be apparent to those skilled in the art that the invention is susceptible to many additional embodiments and that certain of the details described herein can be variued considerably without departing from the basic principles of the invention.

I claim:
1. A device for dispensing a thermally volatilizable substance, comprising:
   a housing;
   a heater secured within the housing and having a heating surface forming a support for a replaceable mat containing the volatilizable substance;
   said housing defining a window over the heating surface and an access opening adjacent to one end of the heating surface for removal and/or insertion or replaceable mats;
   a clamp arm secured to the housing, extending over the window, and terminating in a free end and having means biasing said clamp arm towards the heating surface to press a mat thereagainst; and
   depressible lever secured to the housing and upon depression engageable with the free end of said clamp arm to move the clamp arm away from the heating surface, thereby to release a mat to facilitate removal thereof through said access opening.

2. The device of claim 1 wherein the clamp arm free end and the lever have interacting surfaces whereby depression of the lever results in movement of the clamp arm in a direction normal to the direction of depression.

3. The device of claim 1 wherein said clamp arm has at least one protuberance for engaging a mat.

4. The device of claim 1 wherein the clamp arm and the lever are integrally formed with at least a portion of the housing.

5. The device of claim 1 further including a protective grid secured to the housing and spanning the window, said clamp arm forming a portion of the grid.

6. The device of claim 5 wherein the grid, the clamp arm and the lever are integrally formed with at least a portion of the housing.

7. The device of claim 6 wherein said clamp arm has at least one protuberance for engaging a mat.

8. The device of claim 6 wherein the clamp arm free end and the lever have interacting surfaces whereby depression of the lever results in movement of the clamp arm in a direction normal to the direction of depression.

* * * * *

UNITED STATES PATENT OFFICE
CERTIFICATE OF CORRECTION

Patent No. 4,391,781            Dated July 5, 1983

Inventor(s)   Klaas J. van Lit

It is certified that error appears in the above-identified patent and that said Letters Patent are hereby corrected as shown below:

On the Title Page, in the figure appearing on the lefthand side, the number "38" on the lower lefthand side of the figure should be changed to --39--.

On the Title Page, in the figure appearing on the righthand side, the number "38" on the lower lefthand side of the figure should be changed to --39--.

On Sheet 2 of the drawings, Figure 3, the number "38" on the lower lefthand side of the figure should be changed to --39--.

On Sheet 2 of the drawings, Figure 4, the number "38" on the lower lefthand side of the figure should be changed to --39--.

In Column 1, Line 66, the word "obect" should be changed to --object--.

In Column 3, Line 29, the word "sidwall" should be changed to --sidewall--.

In Column 4, Line 39, the word "variued" should be changed to --varied--.

UNITED STATES PATENT OFFICE
CERTIFICATE OF CORRECTION

Patent No. 4,391,781        Dated July 5, 1983

Inventor(s) Klaas J. van Lit

It is certified that error appears in the above-identified patent and that said Letters Patent are hereby corrected as shown below:

In Column 4, Line 52, the word "or" should be changed to --of--.

In Column 4, Line 57, the word --a-- should be inserted before the word "depressible".

Signed and Sealed this

Sixth Day of December 1983

[SEAL]

Attest:

GERALD J. MOSSINGHOFF

Attesting Officer    Commissioner of Patents and Trademarks